United States Patent

Carati et al.

[11] Patent Number: 5,914,398
[45] Date of Patent: *Jun. 22, 1999

[54] PROCESS FOR THE PREPARATION OF AMIDES FROM OXIMES

[75] Inventors: Angela Carati; Carlo Perego; Leonardo Dalloro, all of Milan; Giordano De Alberti, Varese; Stefano Palmery, Milan, all of Italy

[73] Assignee: Enichem S.p.A, Milan, Italy

[ * ] Notice: This patent is subject to a terminal disclaimer.

[21] Appl. No.: 08/888,235

[22] Filed: Jul. 3, 1997

[30] Foreign Application Priority Data

Jul. 19, 1996 [IT] Italy ................................. MI96A1499

[51] Int. Cl.⁶ .................................................. C07D 201/04
[52] U.S. Cl. ............................................................. 540/536
[58] Field of Search ............................................... 540/536

[56] References Cited

U.S. PATENT DOCUMENTS

| | | | |
|---|---|---|---|
| 4,281,194 | 7/1981 | Armor et al. | 564/267 |
| 4,359,421 | 11/1982 | Bell et al. | 260/239.3 |
| 4,709,024 | 11/1987 | Sato et al. | 540/536 |
| 4,745,221 | 5/1988 | Roffia et al. | 564/267 |
| 5,041,652 | 8/1991 | Padovan et al. | 564/267 |
| 5,625,108 | 4/1997 | Perego et al. | 585/520 |

*Primary Examiner*—Richard L. Raymond
*Assistant Examiner*—Bruck Kifle
*Attorney, Agent, or Firm*—Oblon, Spivak, McClelland, Maier & Neustadt, P.C.

[57] ABSTRACT

Process for the preparation of caprolactam by the catalytic rearrangement of cyclohexanone oxime in which a vapour phase oxime is contacting a catalyst selected from an essentially amorphous, micro-mesoporous silica-alumina having a molar ratio $SiO_2/Al_2O_3$ of 30 to 5000, a surface area of at least 500 $m^2/g$ and a total pore volume of 0.3 to 1.3 ml/g.

9 Claims, No Drawings

PROCESS FOR THE PREPARATION OF AMIDES FROM OXIMES

The present invention relates to a process for the preparation of amides from oximes.

More specifically, the present invention relates to the use of silica-alumina with a high surface area and high pore volume in the catalytic transformation of oximes, such as cyclohexanone oxime, to amides, such as ε-caprolactam (caprolactam), also known as Beckmann catalytic rearrangement.

Amides, in particular caprolactam, are known in literature as important intermediates for chemical syntheses and as raw materials for the preparation of polyamide resins.

Caprolactam is at present produced industrially by cyclohexanone oxime rearrangement in liquid phase using sulfuric acid or oleum. The rearranged product is neutralized with ammonia causing the formation of ammonium sulfate as by-product. This technology has numerous problems linked to the use of sulfuric acid, to the formation of high quantities of ammonium sulfate, with relative problems of disposal, to the corrosion of the equipment owing to the presence of acid vapours, etc.

Alternative processes have been proposed in literature for the catalytic rearrangement of cyclohexanone oxime into caprolactam, in which solids of an acid nature are used as catalysts. Such solids are selected from derivatives of boric acid, zeolites, nonzeolitic molecular sieves, solid phosphoric acid, mixed metal oxides, etc.

In particular, European patent 234.088 describes method for preparing caprolactam in which cyclohexanone oxime in gaseous state is contacting with a crystalline aluminosilicate having a "Constraint Index" of 1 to 12, an atomic ratio Si/Al of at least 500 and an external acid functionality of less than 5 micro equivalent/g.

With the aim of providing another method for the preparation of amides, and in particular of caprolactam, the Applicant has now found a new process which uses an acid catalyst, having particular morphological and structural properties, as described below, characterized by a considerable catalytic activity, a high selectivity, practically regardless of the conversion, and the possibility of being regenerated by thermal treatment.

The present invention therefore relates to a process for the preparation of amides via the catalytic rearrangement of oximes which comprises putting an oxime in vapour phase in contact with a catalyst selected from an essentially amorphous, micro-mesoporous silica-alumina having a molar ratio $SiO_2/Al_2O_3$ of 30 to 5000, a surface area of at least 500 m²/g and a total pore volume of 0.3 to 1.3 ml/g.

Examples of preferred catalysts according to the present invention are silica-alumina amorphous to X-rays, having a molar ratio $SiO_2/Al_2O_3$ of 30 to 1000, preferably between 50 and 500, a surface area (measured with the B.E.T. method by adsorption-desorption cycles of nitrogen, at the temperature of liquid nitrogen (77 K), using a Carlo Erba Sorptomatic 1900 instrument) of more than 500 m²/g, generally between 500 and 1,000 m²/g, a total pore volume of 0.4 to 0.8 ml/g, an average pore diameter of 20 to 40 Å. These materials are known in literature and described, together with the methods for their preparation, in U.S. Pat. No. 5.049.536 or in published European patent application 659.478.

More specifically, according to European patent application 659.478, the amorphous silica-alumina described above can be obtained by preparing an aqueous solution, possibly containing a free alcohol, of:

i) a tetraalkylammonium hydroxide;

ii) a soluble compound of aluminum capable of hydrolyzing and producing $Al_2O_3$, for example an aluminum trialkoxide such as aluminum tri-n-propoxide or aluminum tri-isopropoxide;

iii) a soluble compound of silicon capable of hydrolyzing and producing $SiO_2$, for example a tetraalkyl orthosilicate such as tetra-ethyl orthosilicate.

The solution thus obtained is heated to activate the gelation and the gel thus produced is dried and then calcined.

It has been observed that, if the preparation of amorphous silica-alumina takes place under particular conditions, the materials obtained have a pore volume up to 1.3 ml/g, and over, and an average pore diameter of 20 to 40 Å, the remaining characteristics being kept unvaried, and are active in the Beckmann catalytic rearrangement. These particular conditions are selected from at least one of those described hereunder:

the use of a tetraalkylammonium hydroxide in which the alkyl group is a hexyl or heptyl;

the possible free alcohol added to the reaction medium is selected from $C_2$–$C_6$ alkyl monoalcohols, with molar ratios alcohol/$SiO_2$ of between 0 and 20;

carrying out the gelation at a temperature of between room temperature and the boiling point of the reaction medium.

Also preferred as catalysts are silica-alumina whose X-ray diffraction spectrum from powders (XRD) of the aluminum-silica gel (registered by means of a Philips vertical diffractometer, equipped with a proportional impulse counter, divergent and recipient slides of ⅙° and with Cukα radiation, λ=1.54178 Å) is characterized by the presence of a single widened diffraction line or, however, by a widespread "scattering", at angular values of not more than 2θ=5°, and having a molar ratio $SiO_2/Al_2O_3$ of 30 to 1000, preferably between 50 and 500, a surface area of 500 to 1,200 m²/g, a total pore volume of 0.3 to 1.3 ml/g and an average pore diameter of less than 40 Å. These catalysts are known in literature and described, together with the methods for their preparation, in published European patent application 691.305 or in Italian patent application MI 95/A 712.

According to these methods, and in particular according to the method of European patent application 691.305, the silica-alumina are prepared by subjecting to hydrolysis and gelation a solution of a tetra-alkyl orthosilicate in a $C_2$–$C_6$ alcohol with an aqueous solution of a tetraalkylammonium hydroxide and an aluminum alkoxide at a temperature of 20 to 80° C., and subjecting the gel thus obtained to drying and subsequent calcination.

Further silica-alumina can be obtained by modifying the above preparation by substituting the tetraalkylammonium hydroxide with an amine having the general formula:

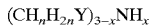

$$(CH_nH_{2n}Y)_{3-x}NH_x$$

wherein n is an integer between 3 and 7, x is zero or is selected from 1 and 2, Y can be H or OH and in which the molar ratios:

$SiO_2/Al_2O_3$ are between 30 and 1000, preferably between 50 and 500;

Amine/$SiO_2$ are between 0.05 and 0.5;

Water/$SiO_2$ are between 1 and 30;

Alcohol/SiO2 are between 0 and 20.

The products thus obtained have a surface area of at least 500 m²/g, a pore volume of 0.3 to 1.3 ml/g, with a widened distribution in the micro-mesoporous region.

According to the present invention the preferred amide is ε-caprolactam (caprolactam) and the preferred oxime is cyclohexanone oxime (CEOX). In particular, the catalytic rearrangement of cyclohexanoneoxime takes place at a pressure of 0.05 to 10 bars and at a temperature of 250 to 500° C., preferably between 300 and 450° C. More specifically, the cyclohexanone oxime, in vapour phase, is fed to the reactor containing the catalyst in the presence of a solvent and optionally an uncondensable gas. The cyclohexanone oxime is dissolved in the solvent and the mixture thus obtained is then vaporized and fed to the reactor.

Preferred solvents are of the type $R_1$-O-$R_2$ wherein $R_1$ is a $C_1$–$C_4$ alkyl chain and $R_2$ can be a hydrogen atom or an alkyl chain containing a number of carbon atoms less than or equal to $R_1$. These solvents can be used alone or mixed with each other or combined with an aromatic hydrocarbon such as benzene or toluene. Alcohols with a $C_1$–$C_2$ alkyl chain are particularly preferred.

The cyclohexanone oxime is fed to the rearrangement reactor with a weight ratio with respect to the catalyst such as to give a WHSV (Weight Hourly Space Velocity), expressed as Kg of cyclohexanone oxime/kg of catalyst/time, of 0.1 to 50 $h^{-1}$, preferably between 0.5 and 20 $h^{-1}$.

The deactivation of the catalyst is due to the formation of organic deposits which block the pores of the catalyst and poison its active sites. The deactivation process is slow and depends on the operating conditions and in particular space velocity, solvent, temperature, composition of the feed. The catalytic activity however can be efficiently reintegrated by the combustion of the organic deposits, by treatment in a stream of air and nitrogen at a temperature of 450 to 600° C.

The following illustrative but non-limiting examples are provided for a better understanding of the present invention and for its embodiment.

EXAMPLES 1–5

Synthesis of catalyst A–E

Catalysts are prepared with a different $SiO_2/Al_2O_3$ ratio [500 (A); 300(B); 200(C); 100(D); 50(E)].

0.8; 1.4; 2.0; 4.1; 8.2 g of $Al(OC_3H_7)_3$ are dissolved respectively in 162 g of an aqueous solution at 12.5% by weight of tetrapropyl ammonium hydroxide (TPAOH). 208 g of $Si(OC_2H_5)_4$ diluted in 368 g of ethanol are then added.

The solution is left under stirring at room temperature until a limpid, homogeneous gel is obtained, which is dried at 100° C. for several hours, then calcined at 550° C. in air for 8 hours. All the products obtained are amorphous to X-rays.

The surface area and pore volume data are shown in Table I.

EXAMPLE 6 (comparative)

Synthesis of catalyst F 208 g of $Si(oC_2H_5)_4$ diluted in 368 g of ethanol are added to 162 g of an aqueous solution at 12.5% by weight of TPAOH.

The solution is left under stirring at room temperature until a limpid, homogeneous gel is obtained, which is dried at 100° C. for several hours, then calcined at 550° C. in air for 8 hours. The product obtained is amorphous to X-rays.

The surface area and pore volume data are shown in Table I.

EXAMPLE 7

Synthesis of catalyst G 290 g of an aqueous solution at 6.9% by weight of TPAOH are charged into a flask equipped with a reflux condenser. The solution is heated and when it has reached 50–60° C. 1.4 g of $Al(OC_3H_7)_3$ are added.

When the aluminum salt has dissolved, the temperature is brought to 98° C., the heating is stopped and 208 g of $Si(OC_2H_5)_4$ are added. When the hydrolysis reaction is complete the temperature spontaneously drops. The mixture is heated again to maintain the temperature at 82–83° C. for one hour and 45 minutes.

The gel obtained is dried at 100° C. and calcined at 550° C. in air for 8 hours. The product is amorphous to X-rays.

The surface area and pore volume data are shown in Table I.

EXAMPLE 8

Synthesis of catalyst X 0.25 g of $Al(OC_3H_7)_3$ are dissolved in 28.9 g of an aqueous solution at 12.5% by weight of TPAOH. 37.8 g of $Si(OC_3H_7)_4$ diluted in 85.9 g of propanol are then added.

After about 45 minutes, a compact opalescent gel is obtained. It is dried at 100° C. for several hours and then calcined at 550° C. in air for 8 hours. The product obtained is amorphous to X-rays.

The surface area and pore volume data are shown in Table I.

EXAMPLE 9 synthesis of catalyst I

Two solutions are prepared. The first contains 102.2 g of ethanol, 11.9 g of $(C_3H_7)_3N$, 27 g of water whereas the second contains 69.4 g of $Si(OC_2H_5)_4$, 51.1 g of ethanol and 0.5 g of $Al(O-secC_4H_9)_3$. The two solutions are mixed together. The mixture is left under stirring at room temperature until a white translucent homogeneous phase is obtained which is dried for several hours at 100° C. and calcined in air at 550° C. for 8 hours.

The surface area and pore volume data are shown in Table I.

EXAMPLE 10

Synthesis of catalyst L

Two solutions are prepared. The first contains 102.2 g of ethanol, 7.4 g of 2-amino-1-butanol, 27 g of water whereas the second contains 69.4 g of $Si(OC_2H_5)_4$, 51.1 g of ethanol and 0.5 g of $Al(O-secC_4H_9)_3$. The two solutions are mixed together. The mixture is left under stirring at room temperature until a white translucent homogeneous phase is obtained which is dried for several hours at 100° C. and calcined in air at 550° C. for 8 hours.

The surface area and pore volume data are shown in Table I.

EXAMPLE 11

Synthesis of catalyst M

Two solutions are prepared. The first contains 38.4 g of an aqueous solution at 7.7% by weight of tetrahexylammonium hydroxide, 148 g of butanol whereas the second contains 52.0 g of $Si(OC_2H_5)_4$, and 0.4 g of $Al(O-secC_4H_9)_3$. The two solutions are mixed together. The mixture is left under stirring at room temperature until a limpid gel is obtained which is dried for several hours at 100° C. and calcined in air at 550° C. for 8 hours.

The surface area and pore volume data are shown in Table I.

TABLE I

| CATALYST | SURFACE AREA (m²/g) | PORE VOLUME (ml/g) |
|---|---|---|
| A | 953 | 0.8 |
| B | 845 | 0.7 |
| C | 575 | 0.4 |
| D | 711 | 0.5 |
| E | 796 | 0.6 |
| F | 598 | 0.4 |
| G | 676 | 0.6 |
| H | 734 | 0.9 |
| I | 656 | 0.9 |
| L | 617 | 0.8 |
| M | 1093 | 1.0 |

EXAMPLE 12

Catalyst A, granulated to 42–80 mesh, is charged into a glass reactor (length 20 cm, internal diameter 1 cm) preheated to 350° C. in nitrogen and dried for 1 hour. A mixture of MeOH/Toluene at a molar ratio of 1/1 is then fed for 30 minutes.

After this pre-treatment, the catalytic test is started by feeding a mixture of CEOX/MeOH/Toluene/$N_2$ preheated and vaporized (WHSV=4.4 $h^{-1}$, molar ratio 1/10/10/8). The temperature of the catalytic bed is maintained at 350° C.

The mixture of the effluent products from the reactor is condensed and analyzed by gaschromatography.

The conversion data of the cyclohexanone oxime and selectivity to caprolactam (CPL) are provided in Table II.

EXAMPLES 13–15

Catalysts B, C and F are tested under the conditions of example 12. The conversion results of the CEOX and selectivity to CPL are shown in Table II.

EXAMPLE 16

A second test is carried out on catalyst B operating as in example 12 but using only MeOH as solvent (WHSV=2.2 $h^{-1}$, CEOX/MeOH/$N_2$=1/40/8) and operating at 380° C.

The conversion of the CEOX and selectivity to CPL are shown in Table II.

EXAMPLES 17–19

Operating as in example 16, catalysts D, E and F are tested.

The conversion of the CEOX and selectivity to CPL are shown in Table II.

TABLE II

| Example | Catalyst | t(h) | % Conv. | % Select. |
|---|---|---|---|---|
| 12 | A | 1 | 48.5 | 75.9 |
|  |  | 20 | 19.1 | 73.2 |
| 13 | B | 1 | 65.1 | 77.9 |
|  |  | 22 | 28.8 | 73.1 |
| 14 | C | 1 | 63.7 | 75.8 |
|  |  | 20 | 14.9 | 77.4 |
| 15 | F | 1 | 7.6 | 74.6 |
|  |  | 20 | 1.2 | 65.5 |
| 16 | B | 1 | 99.7 | 78.3 |
|  |  | 23 | 97.9 | 81.4 |
| 17 | D | 1 | 100.0 | 71.8 |
|  |  | 23 | 98.6 | 78.1 |
| 18 | E | 1 | 100.0 | 71.1 |
|  |  | 21 | 99.2 | 75.8 |
| 19 | F | 1 | 11.8 | 72.0 |
|  |  | 19 | 0.3 | 59.0 |

EXAMPLE 20

Operating as in example 16, catalyst G is tested.

The conversion of the CEOX and selectivity to CPL, after an hour, proved to be 55.2% and 77.8% respectively.

EXAMPLE 21

Catalyst B was tested under the conditions of example 16, adding to the feeding a known quantity of water (molar ratio $H_2O$/CEOX)=0.3.

The data, reported in Table III, that the presence of water in the feed is not critical.

TABLE III

| Example | Solvent | t(h) | % Conv. | % Select. |
|---|---|---|---|---|
| 21 | MeOH/$H_2O$ | 1 | 99.5 | 77.6 |
|  |  | 23 | 96.1 | 80.9 |

EXAMPLES 22–25

Catalyst B was tested under the conditions of example 16 but modifying the solvent used. In particular different relative ratios between Toluene/Methanol/Nitrogen were used in order to modify the partial pressure of the CEOX in the reaction.

The data relating to the feed and reaction products are shown in Table IV.

TABLE IV

| Ex. | Tol/MeOH/$N_2$ | $P_{CEOX}$ | t(h) | % Conv. | % Select. |
|---|---|---|---|---|---|
| 22 | 10/10/8 | 0.034 | 1 | 94.8 | 79.8 |
|  |  |  | 24 | 65.7 | 75.5 |
| 23 | 0/40/8 | 0.020 | 1 | 99.7 | 78.3 |
|  |  |  | 24 | 97.9 | 81.4 |
| 24 | 0/20/32 | 0.019 | 1 | 99.9 | 80.9 |
|  |  |  | 24 | 93.7 | 82.3 |
| 25 | 0/80/8 | 0.011 | 1 | 98.9 | 80.5 |
|  |  |  | 27 | 96.6 | 85.4 |

EXAMPLE 26

Catalyst H was tested under the conditions of example 22. The results are shown in Table V.

TABLE V

| Example | Catalyst | t(h) | % Conv. | % Select. |
|---|---|---|---|---|
| 26 | H | 1 | 99.4 | 79.8 |
|  |  | 24 | 78.1 | 80.6 |

EXAMPLES 27–29

Catalysts I, L and M were tested under the conditions of example 16. The performance of the materials is shown in Table VI.

TABLE VI

| Example | Catalyst | t(h) | % Conv. | % Select. |
|---|---|---|---|---|
| 27 | I | 1 | 99.9 | 86.5 |
|   |   | 21 | 98.9 | 87.1 |
| 28 | L | 1 | 96.9 | 82.0 |
|   |   | 23 | 85.2 | 84.3 |
| 29 | M | 1 | 99.6 | 75.8 |
|   |   | 23 | 97.5 | 79.8 |

EXAMPLE 30

The stability of the performance of catalyst B was evaluated operating under the conditions of example 16. The results are shown in Table VII.

TABLE VII

| t(h) | % Conv. | % Select. |
|---|---|---|
| 1 | 99.7 | 78.3 |
| 3 | 99.6 | 79.7 |
| 5 | 99.3 | 79.5 |
| 14 | 98.2 | 80.0 |
| 23 | 97.9 | 81.4 |
| 27 | 96.0 | 78.8 |
| 29 | 94.9 | 81.3 |
| 38 | 94.8 | 82.4 |
| 47 | 93.7 | 81.5 |
| 48 | 94.1 | 82.2 |

EXAMPLE 31

The stability of the performance of catalyst I was evaluated operating under the conditions of example 16. The results are shown in Table VIII.

TABLE VIII

| t(h) | % Conv. | % Select. |
|---|---|---|
| 1 | 99.9 | 86.5 |
| 2 | 100.0 | 87.5 |
| 10 | 99.6 | 87.7 |
| 19 | 99.5 | 87.3 |
| 21 | 98.9 | 87.1 |
| 23 | 99.0 | 87.3 |
| 25 | 98.8 | 87.3 |
| 34 | 96.9 | 86.8 |
| 43 | 96.5 | 86.6 |
| 44 | 96.4 | 86.8 |

We claim:

1. A process for the preparation of ε-caprolactam via the catalytic rearrangement of oximes which comprises contacting cyclohexanone oxime in vapour phase with a catalyst selected from an essentially amorphous, micro-mesoporous silica-alumina having a molar ratio $SiO_2/Al_2O_3$ of 30 to 5000, a surface area of at least 500 m$^2$/g and a total pore volume of 0.3 to 1.3 ml/g.

2. The process according to claim 1, wherein the catalysts are selected from silica-alumina amorphous to X-rays, having a molar ratio $SiO_2/Al_2O_3$ of 30 to 1000, a surface area, measured with the B.E.T. method of 500 to 1,000 m$^2$/g, a total pore volume of 0.4 to 0.8 ml/g, an average pore diameter of 20 to 40 Å.

3. The process according to claim 1, wherein the catalysts are selected from silica-alumina amorphous to X-rays, having a total pore volume of up to 1.3 ml/g and an average pore diameter of 20 to 40 Å obtained by a process which comprises:

the preparation of an aqueous solution, optionally containing a free alcohol, of:
  i) a tetraalkylammonium hydroxide;
  ii) a soluble compound of aluminum capable of hydrolyzing and producing $Al_2O_2$;
  iii) a soluble compound of silicon capable of hydrolyzing and producing $SiO_2$;
the gelation of the solution; and the drying and calcination of the gel thus produced, said process being characterized in that at least one of the following conditions is satisfied:
the use of a tetraalkylammonium hydroxide in which the alkyl group is a hexyl or heptyl;
the possible free alcohol added to the reaction medium is selected from $C_2$–$C_6$ alkyl monoalcohols, with molar ratios alcohol/$SiO_2$ of 0 to 20;
carrying out the gelation at a temperature of between room temperature and the boiling point of the reaction medium.

4. The process according to claim 1, wherein the catalysts are selected from silica-alumina in which the X-ray diffraction spectrum from powders (XRD) is characterized by the presence of a single widened diffraction line or by a widespread "scattering", at angular values of not more than 2θ=5°, and having a molar ratio $SiO_2/Al_2O_3$ of 30 to 1000, a surface area of 500 to 1,200 m$^2$/g, a total pore volume of 0.3 to 1.3 ml/g and an average pore diameter of less than 40 Å.

5. The process according to claim 1, wherein the catalysts are selected from silica-alumina obtained by subjecting to hydrolysis and gelation a solution of a tetra-alkyl orthosilicate in a $C_2$–$C_6$ alcohol with an aqueous solution of a an aluminum alkoxide and an amine having the general formula:

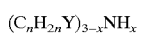

$$(C_nH_{2n}Y)_{3-x}NH_x$$

wherein n is an integer between 3 and 7, x is zero or is selected from 1 and 2, Y can be H or OH and in which the molar ratios:

$SiO_2/Al_2O_3$ are between 30 and 1000;
Amine/$SiO_2$ are between 0.05 and 0.5;
Water/$SiO_2$ are between 1 and 30;
Alcohol/$SiO_2$ Are between 0 and 20.

6. The process according to claim 1, wherein the molar ratio $SiO_2/Al_2O_3$ of the catalyst is between 50 and 500.

7. The process according to claim 1, in which the catalytic rearrangement of the oxime takes place at a pressure of 0.05 to 10 bars and at a temperature of 250 to 500° C.

8. The process according to claim 1, wherein the catalytic rearrangement of the oxime takes place in the presence of a solvent.

9. The process according to claim 8, wherein the solvent is selected from products having the formula $R_1$-O-R wherein $R_1$ is a $C_1$–$C_4$ alkyl chain and $R_2$ is a hydrogen atom or an alkyl chain containing a number of carbon atoms less than or equal to $R_1$.

* * * * *